(12) United States Patent
Liversidge et al.

(10) Patent No.: US 8,367,112 B2
(45) Date of Patent: Feb. 5, 2013

(54) NANOPARTICULATE CARVERDILOL FORMULATIONS

(75) Inventors: Gary Liversidge, West Chester, PA (US); Scott Jenkins, Downingtown, PA (US)

(73) Assignee: Alkermes Pharma Ireland Limited, Dublin (IE)

( * ) Notice: Subject to any disclaimer, the term of this patent is extended or adjusted under 35 U.S.C. 154(b) by 1605 days.

(21) Appl. No.: 11/363,266

(22) Filed: Feb. 28, 2006

(65) Prior Publication Data

US 2007/0202180 A1   Aug. 30, 2007

(51) Int. Cl.
  *A61K 9/14*   (2006.01)
  *A61K 9/16*   (2006.01)
(52) U.S. Cl. ........................................ 424/489; 424/490
(58) Field of Classification Search .................. None
See application file for complete search history.

(56) References Cited

U.S. PATENT DOCUMENTS

| | | | |
|---|---|---|---|
| 4,499,289 A | 2/1985 | Baran et al. |
| 4,503,067 A | 3/1985 | Wiedemann et al. |
| 4,647,576 A | 3/1987 | Hoefle et al. |
| 4,686,237 A | 8/1987 | Anderson |
| 4,783,484 A | 11/1988 | Violante et al. |
| 4,826,689 A | 5/1989 | Violanto et al. |
| 4,997,454 A | 3/1991 | Violante et al. |
| 5,118,528 A | 6/1992 | Fessi et al. |
| 5,145,684 A | 9/1992 | Liversidge et al. |
| 5,177,080 A | 1/1993 | Angerbauer et al. |
| 5,298,262 A | 3/1994 | Na et al. |
| 5,302,401 A | 4/1994 | Liversidge et al. |
| 5,326,552 A | 7/1994 | Na et al. |
| 5,328,404 A | 7/1994 | Bacon |
| 5,336,507 A | 8/1994 | Na et al. |
| 5,346,702 A | 9/1994 | Na et al. |
| 5,349,957 A | 9/1994 | Yudelson |
| 5,352,459 A | 10/1994 | Hollister et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,510,118 A * | 4/1996 | Bosch et al. ................. 424/489 |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |
| 5,534,270 A | 7/1996 | De Castro |
| 5,543,133 A | 8/1996 | Swanson et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,622,938 A | 4/1997 | Wong |
| 5,628,981 A | 5/1997 | Liversidge et al. |
| 5,643,552 A | 7/1997 | Illig |
| 5,665,331 A | 9/1997 | Bagchi et al. |
| 5,718,388 A | 2/1998 | Czekai et al. |
| 5,718,919 A | 2/1998 | Ruddy et al. |
| 5,741,522 A | 4/1998 | Violante et al. |
| 5,747,001 A | 5/1998 | Wiedmann et al. |
| 5,760,069 A | 6/1998 | Lukas-Laskey et al. |
| 5,776,496 A | 7/1998 | Violante et al. |
| 5,834,025 A | 11/1998 | De Garavilla et al. |
| 5,862,999 A | 1/1999 | Czekai et al. |
| 5,902,821 A | 5/1999 | Lukas-Laskey et al. |
| 6,045,829 A | 4/2000 | Liversidge et al. |
| 6,068,858 A | 5/2000 | Liversidge et al. |
| 6,165,506 A | 12/2000 | Jain et al. |
| 6,221,400 B1 | 4/2001 | Liversidge et al. |

(Continued)

FOREIGN PATENT DOCUMENTS

CN   1420771   5/2003
EP   0 142 146 A2   5/1985

(Continued)

OTHER PUBLICATIONS

Agnihotri et al., "Development of novel interpenetrating network gellan gum-poly (vinyl alcohol) hydrogel microspheres for the controlled release of carvedilol", *Drug Development and Industrial Pharmacy*, vol. 31, No. 6, (Jul. 2005), pp. 491-503.
Lindahl et al., "Characterization of Fluids from the Stomach and Proximal Jejunum in Men and Women", *Pharmaceutical Research*, vol. 14, No. 4, pp. 497-502 (1997).
Am. J. Hypertens, 14:27-31, 70-73 (2001).
Sharpe, J., "Benefits of Beta-Blockers for Heart Failure: Proven in 1999, " Lancet, 353:1988-9 (1999).
Califf et al., "Beta-Blocker Therapy for Heart Failure," JAMA, 283: 1335-7 (2000).
McDonagh et al., Epidemiology & Pathophysiology of Heart Failure, Medicine 26:111-5 (1998).
Davies et al., ABC of Heart Failure: Management: Diuretics, ACE Inhibitors and Nitrates, Bonj. 320, 428-31 (2000).
International Preliminary Report on Patentability for International Application No. PCT/US2007/003479, issued on Sep. 2, 2008, 8 pgs.
Chinese Office Action cited in related Chinese Patent Application No. 200780013936.6, dated May 10, 2010.
Notice of Reasons for Rejection in related Japanese Patent Application No. 2008-557272, dated Aug. 9, 2012.

*Primary Examiner* — Susan Tran
(74) *Attorney, Agent, or Firm* — Foley & Lardner LLP

(57) ABSTRACT

The present invention is directed to nanoparticulate carvedilol compositions having improved pharmacokinetic profiles, improved bioavailability, dissolution rates and efficacy. In one embodiment, the nanoparticulate carvedilol composition has an effective average particle size of less than about 2000 nm.

22 Claims, No Drawings

U.S. PATENT DOCUMENTS

| | | |
|---|---|---|
| 6,264,922 B1 | 7/2001 | Wood et al. |
| 6,267,989 B1 | 7/2001 | Liversidge et al. |
| 6,270,806 B1 | 8/2001 | Liversidge et al. |
| 6,316,029 B1 | 11/2001 | Jain et al. |
| 6,365,618 B1 | 4/2002 | Swartz |
| 6,375,986 B1 | 4/2002 | Ryde et al. |
| 6,428,814 B1 | 8/2002 | Bosch |
| 6,431,478 B1 | 8/2002 | Reed et al. |
| 6,432,381 B2 | 8/2002 | Liversidge et al. |
| 6,582,285 B2 | 6/2003 | Czekai et al. |
| 6,592,903 B2 | 7/2003 | Ryde et al. |
| 6,632,832 B2 | 10/2003 | Burman et al. |
| 6,656,504 B1 | 12/2003 | Bosch et al. |
| 6,699,997 B2 | 3/2004 | Hildesheim et al. |
| 6,730,326 B2 | 5/2004 | Beyer et al. |
| 6,742,734 B2 | 6/2004 | Reed et al. |
| 6,745,962 B2 | 6/2004 | Reed et al. |
| 6,811,767 B1 | 11/2004 | Bosch et al. |
| 6,908,626 B2 | 6/2005 | Cooper et al. |
| 6,969,529 B2 | 11/2005 | Bosch et al. |
| 6,976,647 B2 | 12/2005 | Reed et al. |
| 6,991,191 B2 | 1/2006 | Reed et al. |
| 2001/0036959 A1 | 11/2001 | Gabel et al. |
| 2002/0012675 A1 | 1/2002 | Jain et al. |
| 2003/0035836 A1 * | 2/2003 | Shanghvi et al. ............ 424/468 |
| 2003/0054042 A1 | 3/2003 | Liversidge et al. |
| 2004/0151772 A1 * | 8/2004 | Andersen et al. ............ 424/468 |
| 2005/0181015 A1 | 8/2005 | Zhong et al. |

FOREIGN PATENT DOCUMENTS

| | | |
|---|---|---|
| EP | 0 221 025 A1 | 5/1987 |
| EP | 0 491 226 A1 | 6/1992 |
| FR | 2 596 393 A1 | 10/1987 |
| JP | 2002-511413 | 4/2002 |
| JP | 2005-505568 | 2/2005 |
| WO | WO 86/03488 A1 | 6/1986 |
| WO | WO 86/07054 A1 | 12/1986 |
| WO | WO 9814174 A1 * | 4/1998 |
| WO | WO 99/52526 | 10/1999 |
| WO | WO 01/54667 A1 | 8/2001 |
| WO | WO 01/74357 A1 | 10/2001 |
| WO | WO 2004/014304 A2 | 2/2004 |
| WO | WO 2004/032980 A1 | 4/2004 |
| WO | WO 2004/069169 A2 | 8/2004 |
| WO | WO 2007/025274 A2 | 3/2007 |

* cited by examiner

NANOPARTICULATE CARVERDILOL FORMULATIONS

FIELD OF THE INVENTION

This invention is directed to nanoparticulate carvedilol formulations and methods of making and using the formulations. The formulations of the invention are particularly useful in treating high blood pressure (hypertension), congestive heart failure, cancer, viral infections, psychosis-related conditions, and similar conditions.

BACKGROUND OF THE INVENTION

A. Background Regarding Carvedilol

High blood pressure adds to the workload of the heart and arteries. If it continues for a long time, the heart and arteries may not function properly. This can damage the blood vessels of the brain, heart, and kidneys, resulting in a stroke, heart failure, or kidney failure. High blood pressure may also increase the risk of heart attacks. These problems may be less likely to occur if blood pressure is controlled.

Heart failure can be defined as a state in which an abnormality of cardiac function is responsible for failure of the heart to pump blood at a rate commensurate with the requirements of the metabolizing tissues. Symptoms are generally non-specific and include fatigue, dyspnoea, swollen ankles, and exercise intolerance. The overall prevalence of chronic heart failure (CHF) is estimated at 10-20 per 1000 population, with an annual incidence of 1-5 per 1000. Both prevalence and incidence rise with advancing age. McDonagh et al., "Epidemiology and Pathophysiology of Heart Failure," *Medicine*, 26:111-5 (1998). Heart failure is a major cause of morbidity and mortality. Id. CHF is considered to impair the quality of life more than any other chronic medical disorder. Id. Prognosis in patients with CHF depends on severity (as indicated by symptoms and exercise capacity), age and sex, with a poorer prognosis in male patients. Id. Patients with heart failure require life-long treatment. Pharmacological treatment aims to improve both patients' quality of life and survival. Diuretics and angiotensin converting enzyme (ACE) inhibitors, combined with non-pharmacological measures, form the basis of initial treatment. Davies et al., "ABC of Heart Failure: Management: Diuretics, ACE Inhibitors, and Nitrates," *BMJ*, 320:428-31 (2000). Digoxin may be added in selected patients.

There is now substantial clinical data demonstrating the effectiveness of using beta-blockers in patients with CHF resulting from left ventricular systolic dysfunction. Sharpe N., "Benefits of Beta-Blockers for Heart Failure: Proven in 1999," *Lancet*, 353:1988-9 (1999); Califf et al., "Beta-Blocker Therapy for Heart Failure," *JAMA*, 283:1335-7 (2000).

Carvedilol belongs to a group of medicines called beta-adrenergic blocking agents, beta-blocking agents, or, more commonly, beta-blockers. Beta-blockers work by affecting the response to some nerve impulses in certain parts of the body. As a result, they decrease the heart's need for blood and oxygen by reducing its workload. They also help the heart to beat more regularly. Beta-blockers can also reduce some heart arrhythmias.

Carvedilol is used to treat high blood pressure (hypertension). Carvedilol also is used to prevent further worsening of congestive heart failure in combination with other therapies, such as diuretics, digoxin, and ACE inhibitors. It is used to treat left ventricular dysfunction after a heart attack. Left ventricular dysfunction occurs when the left ventricle (the main pumping chamber of the heart) stiffens and enlarges and can cause the lungs to fill with blood. Beta-blockers approved by the U.S. Food and Drug Administration for heart failure include metoprolol (Toprol®-XL) and carvedilol (COREG®). Metoprolol blocks beta-1 receptors. Carvedilol blocks beta-1, beta-2, and alpha-receptors. They are both good for heart failure, although carvedilol lowers blood pressure more.

Carvedilol may also be used for treating other conditions. For example, recently carvedilol has been reported to have anticancer activity. See U.S. Pat. No. 6,632,832 for "Anticancer activity of carvedilol and its isomers," describing the inhibition of epidermal growth factor and platelet-derived growth factor-dependent proliferation of cancer cells utilizing carvedilol and its isomers. Exemplary cancers treated included cancers of the colon, ovary, breast, prostate, pancreas, lung, melanoma, glioblastoma, oral cancer, and leukemias. In addition, WO 98/38986 describes the use of carvedilol for treating and preventing viral infections, and U.S. Pat. No. 6,365,618 for "Novel methods of treating or preventing tardive dyskinesia, tardive dystonia and tardive akathisia using the antipsychotic agent, carvedilol" describes the use of carvedilol in treating psychoses. This reference also teaches that carvedilol is useful for improving the treatment of mental disorders in which dopamine blocking medications are used, such as manic episodes, major depressive episodes and psychoses, particularly schizophrenia and schizoaffective disorder.

Reported adverse events with carvedilol therapy in clinical trials include dizziness (about 1 in 3 patients on carvedilol), bradycardia, hypotension, oedema, upper respiratory infections, fatigue, lightheadedness, shortness of breath, chest pain (about 1 in 7 patients on carvedilol), low heart rate and low blood pressure, diarrhea (about 1 in 7 patients on carvedilol), high blood sugar (resulting in weight gain), impotence (1-2 out of every 50 men in COREG® clinical trials became impotent; the real-life number may be as high as 15% (*Am. J. Hypertens.*, 14:27-31, 70-73 (2001)), depression, nausea, vomiting, back pain, insomnia, or headache.

In the U.S., carvedilol is marketed under the trade name COREG® (GlaxoSmithKline) (in other countries carvedilol is marketed under other trade names, such as Dilitrend™, Dimitone™, Eucardic™, and Kredex™). COREG® is a white, oval, film-coated tablet containing 3.125 mg, 6.25 mg, 12.5 mg, or 25 mg of carvedilol. The 6.25 mg, 12.5 mg, and 25 mg tablets are TILTAB® tablets. Inactive ingredients consist of colloidal silicon dioxide, crospovidone, hypromellose, lactose, magnesium stearate, polyethylene glycol, polysorbate 80, povidone, sucrose, and titanium dioxide.

The dose of carvedilol will be different for different patients. The following information includes only the average doses of carvedilol. For oral dosage form (tablets): (a) Congestive heart failure: Adults—3.125 mg two times a day, taken with food; (b) Hypertension or left ventricular dysfunction after a heart attack: Adults—6.25 mg two times a day, taken with food.

Pharmacokinetics: COREG® (carvedilol) is rapidly and extensively absorbed following oral administration, with absolute bioavailability of approximately 25% to 35% due to a significant degree of first-pass metabolism. Following oral administration, the apparent mean terminal elimination half-life of carvedilol generally ranges from 7 to 10 hours. Plasma concentrations achieved are proportional to the oral dose administered. When administered with food, the rate of absorption is slowed, as evidenced by a delay in the time to reach peak plasma levels, with no significant difference in extent of bioavailability. It is advised that patients take COREG® (carvedilol) with food to minimize the risk of orthostatic hypotension.

Carvedilol undergoes stereoselective first-pass metabolism with plasma levels of R(+)-carvedilol approximately 2 to 3 times higher than S(−)-carvedilol following oral administration in healthy subjects. The mean apparent terminal elimination half-lives for R(+)-carvedilol range from 5 to 9 hours compared with 7 to 11 hours for the S(−)-enantiomer.

B. Background Regarding Nanoparticulate Active Agent Compositions

Nanoparticulate active agent compositions, first described in U.S. Pat. No. 5,145,684 ("the '684 patent"), are particles consisting of a poorly soluble therapeutic or diagnostic agent having adsorbed onto, or associated with, the surface thereof a non-crosslinked surface stabilizer. The '684 patent does not describe nanoparticulate compositions of carvedilol.

Methods of making nanoparticulate active agent compositions are described in, for example, U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate active agent compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive Nanoparticulate Compositions Having Cationic Surface Stabilizers;" U.S. Pat. No. 6,431,478 for "Small Scale Mill;" and U.S. Pat. No. 6,432,381 for "Methods for Targeting Drug Delivery to the Upper and/or Lower Gastrointestinal Tract," U.S. Pat. No. 6,592,903 for "Nanoparticulate Dispersions Comprising a Synergistic Combination of a Polymeric Surface Stabilizer and Dioctyl Sodium Sulfosuccinate," U.S. Pat. No. 6,582,285 for "Apparatus for sanitary wet milling;" U.S. Pat. No. 6,656,504 for "Nanoparticulate Compositions Comprising Amorphous Cyclosporine;" U.S. Pat. No. 6,742,734 for "System and Method for Milling Materials;" U.S. Pat. No. 6,745,962 for "Small Scale Mill and Method Thereof;" U.S. Pat. No. 6,811,767 for "Liquid droplet aerosols of nanoparticulate drugs;" U.S. Pat. No. 6,908,626 for "Compositions having a combination of immediate release and controlled release characteristics;" U.S. Pat. No. 6,969,529 for "Nanoparticulate compositions comprising copolymers of vinyl pyrrolidone and vinyl acetate as surface stabilizers;" U.S. Pat. No. 6,976,647 for "System and Method for Milling Materials;" and U.S. Pat. No. 6,991,191 for "Method of Using a Small Scale Mill;" all of which are specifically incorporated by reference. In addition, U.S. Patent Application No. 20020012675 A1, published on Jan. 31, 2002, for "Controlled Release Nanoparticulate Compositions," describes nanoparticulate compositions and is specifically incorporated by reference.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

There is a need in the art for carvedilol compositions having greater bioavailability, decreased incidence, frequency, or severity of adverse events, decreased dosage quantity, and other improved dosage characteristics. The present invention satisfies these needs.

SUMMARY OF THE INVENTION

The present invention relates to nanoparticulate compositions comprising carvedilol. The compositions comprise carvedilol and at least one surface stabilizer adsorbed on or associated with the surface of the carvedilol particles. The nanoparticulate carvedilol particles have an effective average particle size of less than about 2000 nm. A preferred dosage form of the invention is a solid dosage form, although any pharmaceutically acceptable dosage form can be utilized.

Another aspect of the invention is directed to pharmaceutical compositions comprising a nanoparticulate carvedilol formulation of the invention. The pharmaceutical compositions comprise carvedilol, at least one surface stabilizer, and a pharmaceutically acceptable carrier, as well as any desired excipients.

Another aspect of the invention is directed to a nanoparticulate carvedilol composition having improved pharmacokinetic profiles as compared to conventional microcrystalline or solubilized carvedilol formulations.

In yet another embodiment, the invention encompasses carvedilol compositions wherein administration of the composition to a subject in a fasted state as compared to administration of the composition to a subject in a fed state produces similar rates of absorption.

Another embodiment of the invention is directed to nanoparticulate carvedilol compositions additionally comprising one or more compounds useful in treating hypertension, congestive heart failure, or related conditions.

This invention further discloses a method of making a nanoparticulate carvedilol composition according to the invention. Such a method comprises contacting carvedilol and at least one surface stabilizer for a time and under conditions sufficient to provide a nanoparticulate carvedilol composition. The one or more surface stabilizers can be contacted with carvedilol either before, during, or after size reduction of carvedilol.

The present invention is also directed to methods of using the nanoparticulate carvedilol compositions of the invention for treating or preventing conditions such as hypertension, congestive heart failure, cancer, viral inventions, psychosis-related conditions such as tardive dyskinesia, tardive dystonia and tardive akathisia, and related conditions.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

A. Introduction

The invention is directed to nanoparticulate compositions comprising carvedilol. The compositions comprise carvedilol and preferably at least one surface stabilizer adsorbed on or associated with the surface of the drug. The nanoparticulate carvedilol particles have an effective average particle size of less than about 2000 nm.

Advantages of the nanoparticulate carvedilol formulations of the invention include, but are not limited to: (1) smaller tablet or other solid dosage form size, or less frequent administration of the formulation; (2) smaller doses of drug required to obtain the same pharmacological effect as compared to conventional microcrystalline or solubilized forms of carvedilol; (3) increased bioavailability as compared to conventional microcrystalline or solubilized forms of carvedilol; (4) improved pharmacokinetic profiles, such as $T_{max}$, $C_{max}$, and/or AUC profiles as compared to conventional microcrystalline or solubilized forms of carvedilol; (5) substantially similar pharmacokinetic profiles of the nanoparticulate carvedilol compositions when administered in the fed versus the fasted state; (6) bioequivalent pharmacokinetic profiles of the nanoparticulate carvedilol compositions when administered in the fed versus the fasted state; (7) an increased rate of dissolution for the nanoparticulate carvedilol compositions as compared to conventional microcrystalline or solubilized forms of carvedilol; (8) bioadhesive carvedilol compositions; (9) decreased incidence, frequency, or severity of adverse events as compared to conventional microcrystalline or solubilized forms of carvedilol; and (10) use of the nanoparticulate carvedilol compositions in conjunction with other active agents useful in treating hypertension, congestive heart failure, and related conditions.

The present invention also includes nanoparticulate carvedilol compositions together with one or more non-toxic physiologically acceptable carriers, adjuvants, or vehicles, collectively referred to as carriers. The compositions can be formulated for oral administration in solid, liquid, or aerosol form, parenteral injection (e.g., intravenous, intramuscular, or subcutaneous), vaginal, nasal, rectal, ocular, local (powders, ointments or drops), buccal, intracisternal, intraperitoneal, or topical administration, and the like. A preferred dosage form of the invention is a solid dosage form for oral administration, although any pharmaceutically acceptable dosage form can be utilized. Exemplary solid dosage forms include, but are not limited to, tablets, capsules, sachets, lozenges, powders, pills, or granules.

The dosage forms of the invention, including solid dosage forms, can be, for example, a fast melt dosage form, controlled release dosage form, lyophilized dosage form, delayed release dosage form, extended release dosage form, pulsatile release dosage form, mixed immediate release and controlled release dosage form, or a combination thereof. A solid dose tablet formulation is preferred.

B. Definitions

The present invention is described herein using several definitions, as set forth below and throughout the application.

The term "effective average particle size", as used herein means that at least 50% of the nanoparticulate carvedilol particles have a particle size, by weight, of less than about 2000 nm when measured by, for example, sedimentation field flow fractionation, photon correlation spectroscopy, light scattering, disk centrifugation, and other techniques known to those of skill in the art.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein with reference to a "stable" carvedilol particle, this term connotes, but is not limited to, one or more of the following parameters: (1) carvedilol particles do not appreciably flocculate or agglomerate due to interparticle attractive forces or otherwise significantly increase in particle size over time; (2) that the physical structure of the carvedilol particles is not altered over time, such as by conversion from an amorphous phase to a crystalline phase; (3) that the carvedilol particles are chemically stable; and/or (4) where carvedilol has not been subject to a heating step at or above the melting point of carvedilol in the preparation of the nanoparticles of the invention.

The term "conventional" or "non-nanoparticulate active agent" shall mean an active agent which is solubilized or which has an effective average particle size of greater than about 2000 nm. Nanoparticulate active agents as defined herein have an effective average particle size of less than about 2000 nm.

The phrase "poorly water soluble drugs" as used herein refers to those drugs that have a solubility in water of less than about 30 mg/ml, preferably less than about 20 mg/ml, preferably less than about 10 mg/ml, or preferably less than about 1 mg/ml.

As used herein, the phrase "therapeutically effective amount" shall mean that drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art.

C. Preferred Characteristics of the Nanoparticulate Carvedilol Compositions

There are a number of enhanced pharmacological characteristics of nanoparticulate carvedilol compositions of the invention.

1. Increased Bioavailability

In one embodiment of the invention, the carvedilol formulations of the invention exhibit increased bioavailability at the same dose, and require smaller doses as compared to prior conventional carvedilol formulations (e.g., COREG®). Moreover, a nanoparticulate carvedilol dosage form requires less drug to obtain the same pharmacological effect observed with a conventional microcrystalline carvedilol dosage form (e.g., COREG®). Therefore, the nanoparticulate carvedilol dosage form has an increased bioavailability as compared to the conventional microcrystalline carvedilol dosage form.

2. The Pharmacokinetic Profiles of the Carvedilol Compositions of the Invention are not Affected by the Fed or Fasted State of the Subject Ingesting the Compositions In another embodiment of the invention, the pharmacokinetic profile of the carvedilol in the nanoparticulate carvedilol compositions is not substantially affected by the fed or fasted state of a subject ingesting the composition. This means that there is little or no appreciable difference in the quantity of drug absorbed or the rate of drug absorption when the nanoparticulate carvedilol compositions are administered in the fed versus the fasted state.

Benefits of a dosage form which substantially eliminates the effect of food include an increase in subject convenience, thereby increasing subject compliance, as the subject does not need to ensure that they are taking a dose either with or without food. This is significant, as with poor subject compliance an increase in the medical condition for which the drug is being prescribed may be observed, i.e., hypertension or congestive heart failure for poor subject compliance with carvedilol.

The invention also provides carvedilol compositions having a desirable pharmacokinetic profile when administered to mammalian subjects. The desirable pharmacokinetic profile of the carvedilol compositions preferably includes, but is not limited to: (1) a $C_{max}$ for carvedilol, when assayed in the plasma of a mammalian subject following administration, that is preferably greater than the $C_{max}$ for a non-nanoparticulate carvedilol formulation (e.g., COREG®), administered at the same dosage; and/or (2) an AUC for carvedilol, when assayed in the plasma of a mammalian subject following administration, that is preferably greater than the AUC for a non-nanoparticulate carvedilol formulation (e.g., COREG®), administered at the same dosage; and/or (3) a Tmax for carvedilol, when assayed in the plasma of a mammalian subject following administration, that is preferably less than the Tmax for a non-nanoparticulate carvedilol formulation (e.g., COREG®), administered at the same dosage. The desirable pharmacokinetic profile, as used herein, is the pharmacokinetic profile measured after the initial dose of carvedilol.

In one embodiment, the nanoparticulate carvedilol composition exhibits in comparative pharmacokinetic testing with a non-nanoparticulate carvedilol formulation (e.g., COREG®), administered at the same dosage, a $T_{max}$ not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the $T_{max}$ exhibited by the non-nanoparticulate carvedilol formulation.

In another embodiment, the nanoparticulate carvedilol composition exhibits in comparative pharmacokinetic testing with a non-nanoparticulate carvedilol formulation of (e.g., COREG®), administered at the same dosage, a $C_{max}$ which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the $C_{max}$ exhibited by the non-nanoparticulate carvedilol formulation.

In yet another embodiment, the nanoparticulate carvedilol composition exhibits in comparative pharmacokinetic testing with a non-nanoparticulate carvedilol formulation (e.g., COREG®), administered at the same dosage, an AUC which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by the non-nanoparticulate carvedilol formulation (e.g., COREG®).

3. Bioequivalency of the Carvedilol Compositions of the Invention when Administered in the Fed Versus the Fasted State In one embodiment of the invention, the invention encompasses a composition comprising nanoparticulate carvedilol in which administration of the composition to a subject in a fasted state is bioequivalent to administration of the composition to a subject in a fed state. The difference in absorption of the compositions comprising the nanoparticulate carvedilol when administered in the fed versus the fasted state, is preferably less than about 35%, less than about 30%, less than about 25%, less than about 20%, less than about 15%, less than about 10%, less than about 5%, or less than about 3%.

In one embodiment of the invention, the invention encompasses nanoparticulate carvedilol wherein administration of the composition to a subject in a fasted state is bioequivalent to administration of the composition to a subject in a fed state, in particular as defined by $C_{max}$ and AUC guidelines given by the U.S. Food and Drug Administration and the corresponding European regulatory agency (EMEA). Under U.S. FDA guidelines, two products or methods are bioequivalent if the 90% Confidence Intervals (CI) for AUC and $C_{max}$ are between 0.80 to 1.25 ($T_{max}$ measurements are not relevant to bioequivalence for regulatory purposes). To show bioequivalency between two compounds or administration conditions pursuant to Europe's EMEA guidelines, the 90% CI for AUC must be between 0.80 to 1.25 and the 90% CI for $C_{max}$ must between 0.70 to 1.43.

4. Dissolution Profiles of the Carvedilol Compositions of the Invention

In another embodiment of the invention, the carvedilol compositions of the invention have unexpectedly dramatic dissolution profiles. Rapid dissolution of carvedilol following administration is preferable, as faster dissolution generally leads to faster onset of action and greater bioavailability. To improve the dissolution profile and bioavailability of carvedilol, it is useful to increase the drug's dissolution so that it could attain a level close to 100%.

The carvedilol compositions of the invention preferably have a dissolution profile in which within about 5 minutes at least about 20% of the composition is dissolved. In other embodiments of the invention, at least about 30% or at least about 40% of the carvedilol composition is dissolved within about 5 minutes. In yet other embodiments of the invention, at least about 40%, at least about 50%, at least about 60%, at least about 70%, or at least about 80% of the carvedilol composition is dissolved within about 10 minutes. Finally, in another embodiment of the invention, at least about 70%, at least about 80%, at least about 90%, or at least about 100% of the carvedilol composition is dissolved within about 20 minutes.

Dissolution is preferably measured in a medium which is discriminating. Such a dissolution medium will produce two very different dissolution curves for two products having very different dissolution profiles in gastric juices, i.e., the dissolution medium is predictive of in vivo dissolution of a composition. An exemplary dissolution medium is an aqueous medium containing the surfactant sodium lauryl sulfate at 0.025 M. Determination of the amount dissolved can be carried out by spectrophotometry. The rotating blade method (European Pharmacopoeia) can be used to measure dissolution.

5. Redispersibility Profiles of the Carvedilol Compositions of the Invention

In one embodiment of the invention, the nanoparticulate carvedilol compositions redisperse such that the effective average particle size of the redispersed carvedilol particles is less than about 2 microns. This is significant, as if upon administration the nanoparticulate carvedilol compositions of the invention did not redisperse to a nanoparticulate particle size, then the dosage form may lose the benefits afforded by formulating carvedilol into a nanoparticulate particle size. A nanoparticulate size suitable for the present invention is an effective average particle size of less than about 2000 nm.

Indeed, the nanoparticulate carvedilol compositions of the invention benefit from the small particle size of carvedilol; if carvedilol does not redisperse into a small particle size upon administration, then "clumps" or agglomerated carvedilol particles are formed, owing to the extremely high surface free energy of the nanoparticulate system and the thermodynamic driving force to achieve an overall reduction in free energy. With the formation of such agglomerated carvedilol particles, the bioavailability of the carvedilol dosage form can drop significantly.

Moreover, the nanoparticulate carvedilol compositions of the invention exhibit dramatic redispersion of the nanoparticulate carvedilol particles upon administration to a mammal, such as a human or animal, as demonstrated by reconstitution/redispersion in a biorelevant aqueous media such that the effective average particle size of the redispersed carvedilol particles is less than about 2 microns. Such biorelevant aqueous media can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1M while fasted state intestinal fluid has an ionic strength of about 0.14. See e.g., Lindahl et al., "Characterization of Fluids from the Stomach and Proximal Jejunum in Men and Women," *Pharm. Res.*, 14 (4): 497-502 (1997). It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 N, and NaCl solutions, ranging in concentration from about 0.001 to about 0.1 M, and mixtures thereof. For example, electrolyte solutions can be, but are not limited to, about 0.1 N HCl or less, about 0.01 N HCl or less, about 0.001 N HCl or less, about 0.1 M NaCl or less, about 0.01 M NaCl or less, about 0.001 M NaCl or less, and mixtures thereof. Of these electrolyte solutions, 0.01 N HCl and/or 0.1 M NaCl, are most representative of fasted human physiological conditions, owing to the pH and ionic strength conditions of the proximal gastrointestinal tract.

Electrolyte concentrations of 0.001 N HCl, 0.01 N HCl, and 0.1 N HCl correspond to pH 3, pH 2, and pH 1, respectively. Thus, a 0.01 N HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+sodium, potassium and calcium salts of chloride.

In other embodiments of the invention, the redispersed carvedilol particles of the invention (redispersed in an aqueous, biorelevant, or any other suitable media) have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

Redispersibility can be tested using any suitable means known in the art. See e.g., the example sections of U.S. Pat. No. 6,375,986 for "Solid Dose Nanoparticulate Compositions Comprising a Synergistic Combination of a Polymeric Surface Stabilizer and Dioctyl Sodium Sulfosuccinate."

6. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, are colloidal silicon dioxide, such as Aerosil® 200, talc, stearic acid, magnesium stearate, calcium stearate, and silica gel. Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride. Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof. Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

7. Combination Pharmacokinetic Profile Compositions

In yet another embodiment of the invention, a first nanoparticulate carvedilol composition providing a desired pharmacokinetic profile is co-administered, sequentially administered, or combined with at least one other carvedilol composition that generates a desired different pharmacokinetic profile. More than two carvedilol compositions can be co-administered, sequentially administered, or combined. While the first carvedilol composition has a nanoparticulate particle size, the additional one or more carvedilol compositions can be nanoparticulate, solubilized, or have a microparticulate particle size.

The second, third, fourth, etc., carvedilol composition can differ from the first and from each other, for example: (1) in the effective average particle sizes of carvedilol; or (2) in the dosage of carvedilol. Such a combination composition can reduce the dose frequency required. If the second carvedilol composition has a nanoparticulate particle size, then preferably the carvedilol particles of the second composition have at least one surface stabilizer associated with the surface of the drug particles. The one or more surface stabilizers can be the same as or different from the surface stabilizer(s) present in the first carvedilol composition.

Preferably where co-administration of a "fast-acting" formulation and a "longer-lasting" formulation is desired, the two formulations are combined within a single composition, for example a dual-release composition.

8. Controlled Release Nanoparticulate Carvedilol Compositions

In one embodiment of the invention, the nanoparticulate carvedilol compositions are formulated into a controlled release dosage form. Controlled release profiles include, for example, sustained release, prolonged release, pulsatile release, and delayed release profiles. In contrast to immediate release compositions, controlled release carvedilol compositions allow delivery of carvedilol to a subject over an extended period of time according to a predetermined profile. Such release rates can provide therapeutically effective levels of carvedilol for an extended period of time and thereby provide a longer period of pharmacologic or diagnostic response as compared to conventional rapid release dosage forms. Such longer periods of response provide for many inherent benefits that are not achieved with the corresponding short acting, immediate release preparations.

Controlled release dosage forms of nanoparticulate active agents are described in U.S. Patent Application No. 20020012675 A1 for "Controlled Release Nanoparticulate Compositions," which is specifically incorporated by reference. Typically, a controlled release carvedilol composition comprises nanoparticulate carvedilol, at least one surface stabilizer, and at least one rate controlling polymer. The type of rate controlling polymer depends upon the type of rate controlling dosage form utilized.

There are several different types of rate controlling dosage forms. In a first aspect of the invention, the nanoparticulate carvedilol, at least one surface stabilizer, and one or more auxiliary excipient materials are compressed into a tablet form followed by coating with a rate controlling polymer material. In a second aspect, the nanoparticulate carvedilol, at least one surface stabilizer, a rate controlling polymer material, and one or more auxiliary excipients are compressed together to form a controlled release matrix. The controlled release matrix may optionally be coated with a rate controlling polymer to provide additional controlled release properties. In a third aspect, the nanoparticulate carvedilol, at least one surface stabilizer, and one or more auxiliary excipient materials are compressed into the form of a multilayer tablet prior to coating with a rate controlling polymer material. In a fourth aspect, the nanoparticulate carvedilol and at least one surface stabilizer are dispersed in a rate controlling polymer material and compressed into a multilayer tablet. The multilayer tablet may optionally be coated with a rate controlling polymer material to provide additional controlled release properties. In an alternative aspect, a first layer in such a multilayer tablet comprises a controlled release composition according to the invention and a second layer comprises a conventional active agent containing composition (e.g., carvedilol or a different active agent), such as an instant release composition. In a fifth aspect, the nanoparticulate carvedilol and at least one surface stabilizer are incorporated into a single layer or multilayer tablet comprising osmagent surrounded by a semi-permeable membrane, with the semi-permeable membrane defining an orifice. In this embodiment the semi-permeable membrane is permeable to aqueous media, such as gastrointestinal fluids, but it is not permeable to the poorly soluble carvedilol when in solution or when in other form. Such osmotic delivery systems are well known in the art, wherein infusion of fluid through the semi-permeable membrane causes the osmagent to swell thus driving the carvedilol through the orifice defined by the semi-permeable membrane. In a sixth aspect, the nanoparticulate carvedilol, at least one surface stabilizer, one or more auxiliary excipients, and a rate controlling polymer material are combined into a multiparticulate form. The multiparticulate form preferably comprises discrete particles, pellets, mini-tablets, or combinations thereof. In a final oral dosage form the multiparticulate form may be encapsulated, for example in hard or soft gelatin capsules. Alternatively, a multiparticulate form may be incorporated into other final dosage forms such as a sachet. In the case of a multiparticulate form comprising discrete particles or pellets, the multiparticulate form may be compressed, optionally with additional auxiliary excipients, into the form of tablets. The compressed multiparticulate tablet may optionally be coated with rate controlling polymer material so as to provide additional controlled release properties.

The choice of a rate controlling polymer first depends upon the type of controlled release system to be utilized: i.e., a coating system or a matrix system. A rate controlling composition utilizing a coating system employs a polymer that forms a water insoluble backbone, such as poly(alkylmethacrylate), as a rate controlling polymer. Water soluble polymers, such as polyvinylpyrrolidone (PVP) and polyethylene glycol (PEG), can also be used in coating systems, but they must be used in conjunction with a polymer that forms a water insoluble backbone to yield a controlled release composition. Thus, if the water soluble polymers PVP and PEG are utilized in a coating system in the absence of a polymer that forms a water insoluble backbone, the resulting composition is an immediate release composition.

Matrix controlled release systems can use as a rate controlling polymer a water soluble polymer having a molecular weight high enough to form a viscous hydrogel. Water soluble polymers such as hydroxypropyl cellulose (HPC) and hydroxypropylmethyl cellulose (HPMC) have varying "grades" or molecular weights; high molecular weight polymers are very viscous, and strong, viscous gels resulting from such polymers control the diffusion of water and drug release, producing rate controlling properties. See "Formulating for Controlled Release with METHOCEL Premium Cellulose Ethers," The Dow Chemical Company (1995).

Exemplary rate-controlling polymers include but are not limited to hydrophilic polymers, hydrophobic polymers, and mixtures of hydrophobic and hydrophilic polymers that are capable of retarding the release of carvedilol from a composition or dosage form of the invention. Particularly useful rate-controlling polymers for causing an effective controlled release of carvedilol following administration include plant exudates (gum arabic), seaweed extracts (agar), plant seed gums or mucilages (guar gum), cereal gums (starches), fermentation gums (dextran), animal products (gelatin), hydroxyalkyl celluloses such as hydroxypropyl cellulose (HPC), hydroxyethyl cellulose (HEC), hydroxypropyl methylcelluose (HPMC), and sodium carboxymethylcellulose (CMC), guar, pectin, and carrageenan. Additional polymers include poly(ethylene) oxide, alkyl cellulose such as ethyl cellulose and methyl cellulose, carboxymethyl cellulose, hydrophilic cellulose derivatives, polyethylene glycol, polyvinylpyrrolidone, cellulose acetate, cellulose acetate butyrate, cellulose acetate phthalate, cellulose acetate trimellitate, polyvinyl acetate phthalate, hydroxypropylmethyl cellulose phthalate, hydroxypropylmethyl cellulose acetate succinate, polyvinyl acetaldiethylamino acetate, poly (alkylmethacrylate) and poly(vinyl acetate). Other suitable hydrophobic polymers include polymers and/or copolymers derived from acrylic or methacrylic acid and their respective esters, waxes, shellac, and hydrogenated vegetable oils. Two or more rate-controlling polymers can be used in combination. The polymers are commercially available and/or can be prepared by techniques known in the art.

9. Carvedilol Compositions Used in Conjunction with Other Active Agents

The carvedilol compositions of the invention can additionally comprise one or more non-carvedilol compounds useful in treating hypertension, congestive heart failure (or related conditions such as dyslipidemia, hyperlipidemia, hypercholesterolemia, and cardiovascular disorders), viral infections, cancer, psychoses, or related conditions. The compositions of the invention can be co-formulated with such other active agents, or the compositions of the invention can be co-administered or sequentially administered in conjunction with such active agents.

Examples of such compounds include, but are not limited to, digoxin, CETP (cholesteryl ester transfer protein) inhibitors (e.g., torcetrapib), cholesterol lowering compounds (e.g., ezetimibe (Zetia®)) antihyperglycemia agents, statins or HMG CoA reductase inhibitors, antihypertensives, ACE inhibitors, and nitrates.

Examples of antihypertensives include, but are not limited to diuretics ("water pills"), beta blockers, alpha blockers, alpha-beta blockers, sympathetic nerve inhibitors, angiotensin converting enzyme (ACE) inhibitors, calcium channel blockers, angiotensin receptor blockers (formal medical name angiotensin-2-receptor antagonists, known as "sartans" for short).

Examples drugs useful in treating hyperglycemia include, but are not limited to, (a) insulin (Humulin®, Novolin®), (b) sulfonylureas, such as glyburide (Diabeta®, Micronase®), acetohexamide (Dymelor®), chlorpropamide (Diabinese®), glimepiride (Amaryl®), glipizide (Glucotrol®), gliclazide, tolazamide (Tolinase®), and tolbutamide (Orinase®), (c) meglitinides, such as repaglinide (Prandin®) and nateglinide (Starlix®), (d) biguanides such as metformin (Glucophage®, Glycon), (e) thiazolidinediones such as rosiglitazone (Avandia®) and pioglitazone (Actos®), and (f) glucosidase inhibitors, such as acarbose (Precose®) and miglitol (Glyset®).

Examples of statins or HMG CoA reductase inhibitors include, but are not limited to, lovastatin (Mevacor®, Altocor®); pravastatin (Pravachol®); simvastatin (Zocor®); velostatin; atorvastatin (Lipitor®) and other 6-[2-(substituted-pyrrol-1-yl)alkyl]pyran-2-ones and derivatives, as disclosed in U.S. Pat. No. 4,647,576); fluvastatin (Lescol®); fluindostatin (Sandoz XU-62-320); pyrazole analogs of mevalonolactone derivatives, as disclosed in PCT application WO 86/03488; rivastatin (also known as cerivastatin, Baycol®) and other pyridyldihydroxyheptenoic acids, as disclosed in European Patent 491226A; Searle's SC-45355 (a 3-substituted pentanedioic acid derivative); dichloroacetate; imidazole analogs of mevalonolactone, as disclosed in PCT application WO 86/07054; 3-carboxy-2-hydroxy-propane-phosphonic acid derivatives, as disclosed in French Patent No. 2,596,393; 2,3-di-substituted pyrrole, furan, and thiophene derivatives, as disclosed in European Patent Application No. 0221025; naphthyl analogs of mevalonolactone, as disclosed in U.S. Pat. No. 4,686,237; octahydronaphthalenes, such as those disclosed in U.S. Pat. No. 4,499,289; keto analogs of mevinolin (lovastatin), as disclosed in European Patent Application No. 0,142,146 A2; phosphinic acid compounds; rosuvastatin (Crestor®); pitavastatin (Pitava®), as well as other HMG CoA reductase inhibitors.

D. Compositions

The invention provides compositions comprising nanoparticulate carvedilol particles and at least one surface stabilizer. The surface stabilizers are preferably adsorbed to or associated with the surface of the carvedilol particles. Surface stabilizers useful herein do not chemically react with the carvedilol particles or itself. Preferably, individual molecules of the surface stabilizer are essentially free of intermolecular cross-linkages. The compositions can comprise two or more surface stabilizers.

The present invention also includes nanoparticulate carvedilol compositions together with one or more non-toxic physiologically acceptable carriers, adjuvants, or vehicles, collectively referred to as carriers. The compositions can be formulated for parenteral injection (e.g., intravenous, intramuscular, or subcutaneous), oral administration in solid, liquid, or aerosol form, vaginal, nasal, rectal, ocular, local (powders, ointments or drops), buccal, intracisternal, intraperitoneal, or topical administration, and the like.

1. Carvedilol

Carvedilol can be in a crystalline phase, an amorphous phase, a semi-crystalline phase, a semi-amorphous phase, or a mixtures thereof. As used herein, the term "carvedilol" encompasses a racemic mixture, isomers of carvedilol, such as R(+)-carvedilol and/or S(−)-carvedilol, including optically active isomers, hydroxy carbazole derivatives of carvedilol, pharmaceutically acceptable salts of carvedilol, and derivatives thereof.

Carvedilol is a nonselective b-adrenergic blocking agent with $a_1$-blocking activity. It is (±)-1-(Carbazol-4-yloxy)-3-[[2-(o-methoxyphenoxy) ethyl]amino]-2-propanol. It is a racemic mixture with the following structure:

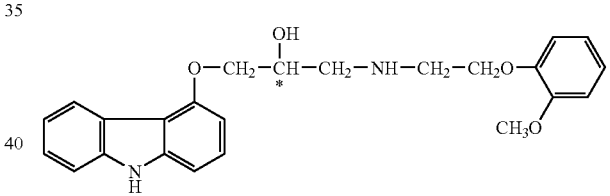

Carvedilol is a white to off-white powder with a molecular weight of 406.5 and a molecular formula of $C_{24}H_{26}N_2O_4$. It is freely soluble in dimethylsulfoxide; soluble in methylene chloride and methanol; sparingly soluble in 95% ethanol and isopropanol; slightly soluble in ethyl ether; and practically insoluble in water, gastric fluid (simulated, TS, pH 1.1), and intestinal fluid (simulated, TS without pancreatin, pH 7.5).

Carvedilol, isomers thereof, or derivatives thereof can be made according to established procedures, such as those detailed in U.S. Pat. Nos. 4,503,067; 5,760,069; 5,902,821; 6,699,997, and 6,730,326, all of which are specifically incorporated by reference.

2. Surface Stabilizers

Preferably, the nanoparticulate carvedilol compositions of the invention comprise at least one surface stabilizer. Combinations of more than one surface stabilizer can be used in the invention.

Useful surface stabilizers that can be employed in the invention include, but are not limited to, known organic and inorganic pharmaceutical excipients. Such excipients include various polymers, low molecular weight oligomers, natural products, and surfactants. Exemplary surface stabilizers include nonionic, ionic, anionic, cationic, and zwitterionic surfactants.

Representative examples of surface stabilizers include hydroxypropyl methylcellulose (now known as hypromellose), hydroxypropylcellulose, polyvinylpyrrolidone, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hypromellose phthalate, noncrystalline cellulose, magnesium aluminium silicate, triethanolamine, polyvinyl alcohol (PVA), 4-(1,1,3, 3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-1OG® or Surfactant 10-G (Olin Chemicals, Stamford, Conn.); Crodestas SL-40® (Croda, Inc.); and SA9OHCO, which is $C_{18}H_{37}CH_2(CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, such as Plasdone® S630, and the like.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$) dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly [diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Nonpolymeric surface stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;

(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where $n>1$;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;
(xi) two of $R_1$-$R_4$ are $CH_3$ and one of $R_1$-$R_4$ is a phenyl ring; or
(xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Particularly preferred surface stabilizers include, but are not limited to, polymeric surface stabilizers, particularly when in combination with sodium lauryl sulfate and/or dioctyl sodium sulfosuccinate (DOSS), hydroxypropyl cellulose (HPC), hydroxypropylmethyl cellulose (HPMC), polyvinylpyrrolidone, Plasdone® S-630, which is a random copolymer of vinyl acetate and vinyl pyrrolidone, and combinations thereof.

The surface stabilizers are commercially available and/or can be prepared by techniques known in the art. Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), and is specifically incorporated herein by reference.

3. Nanoparticulate Carvedilol Particle Size

The compositions of the invention comprise nanoparticulate carvedilol particles which have an effective average particle size of less than about 2000 nm (i.e., 2 microns), less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

By "an effective average particle size of less than about 2000 nm" it is meant that at least 50% of the carvedilol particles have a particle size of less than the effective average, by weight, i.e., less than about 2000 nm, 1900 nm, 1800 nm, etc. (as listed above), when measured by the above-noted techniques. In other embodiments of the invention, at least about 70%, at least about 80%, at least about 90%, at least about 95%, or at least about 99% of the carvedilol particles, by weight, have a particle size of less than the effective average, i.e., less than about 2000 nm, 1900 nm, 1800 nm, 1700 nm, etc.

In the invention, the value for D50 of a nanoparticulate carvedilol composition is the particle size below which 50% of the carvedilol particles fall, by weight. Similarly, D90 is the particle size below which 90% of the carvedilol particles fall, by weight, and D99 is the particle size below which 99% of the carvedilol particles fall, by weight.

4. Concentration of Carvedilol and Surface Stabilizers

The relative amounts of carvedilol and one or more surface stabilizers can vary widely. The optimal amount of the individual components can depend, for example, upon the particular surface stabilizer selected, the hydrophilic lipophilic balance (HLB), melting point, and the surface tension of water solutions of the stabilizer, etc.

In one embodiment, the concentration of carvedilol can vary from about 99.5% to about 0.001%, from about 95% to about 0.1%, or from about 90% to about 0.5%, by weight, based on the total combined weight of carvedilol and at least one surface stabilizer, not including other excipients.

In another embodiment, the concentration of at least one surface stabilizer can vary from about 0.5% to about 99.999%, from about 5.0% to about 99.9%, or from about 10% to about 99.5%, by weight, based on the total combined dry weight of carvedilol and at least one surface stabilizer, not including other excipients.

E. Methods of Making Carvedilol Formulations

In another aspect of the invention there is provided a method of preparing the nanoparticulate carvedilol formulations of the invention. The method generally comprises of one of the following methods: milling, precipitation, homogenization, evaporation, supercritical fluids, or a combination thereof. Exemplary methods of making nanoparticulate active agent compositions are described in U.S. Pat. No. 5,145,684. Methods of making nanoparticulate active agent compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents' with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

Following preparation of a nanoparticulate carvedilol composition by milling, homogenization, precipitation, supercritical fluid particle preparation, etc., the resultant carvedilol composition can be utilized in a suitable dosage form for administration.

For milling and homogenization, preferably the dispersion media used for the size reduction process is aqueous. However, any media in which carvedilol is poorly soluble and dispersible can be used as a dispersion media. Non-aqueous examples of dispersion media include, but are not limited to, aqueous salt solutions, safflower oil and solvents such as ethanol, t-butanol, hexane, and glycol.

Effective methods of providing mechanical force for particle size reduction of carvedilol include but are not limited to ball milling, media milling, and homogenization, for example, with a Microfluidizer® (Microfluidics Corp.). Ball milling is a low energy milling process that uses milling media, drug, stabilizer, and liquid. The materials are placed in a milling vessel that is rotated at optimal speed such that the media cascades and reduces the drug particle size by impaction. The media used must have a high density as the energy for the particle reduction is provided by gravity and the mass of the attrition media.

Media milling is a high energy milling process. Carvedilol, surface stabilizer, and liquid are placed in a reservoir and recirculated in a chamber containing media and a rotating shaft/impeller. The rotating shaft agitates the media which subjects carvedilol to impaction and sheer forces, thereby reducing the carvedilol particle size.

Homogenization is a technique that does not use milling media. Carvedilol, surface stabilizer, and liquid (or carvedilol and liquid with the surface stabilizer added after carvedilol particle size reduction) constitute a process stream propelled into a process zone, which in the Microfluidizer® is called the Interaction Chamber. The product to be treated is inducted into the pump, and then forced out. The priming valve of the Microfluidizer® purges air out of the pump. Once the pump is filled with product, the priming valve is closed and the product is forced through the interaction chamber. The geometry of the interaction chamber produces powerful forces of sheer, impact, and cavitation which are responsible for carvedilol particle size reduction. Specifically, inside the interaction chamber, the pressurized product is split into two streams and accelerated to extremely high velocities. The formed jets are then directed toward each other and collide in the interaction zone. The resulting product has very fine and uniform particle or droplet size. The Microfluidizer® also provides a heat exchanger to allow cooling of the product. U.S. Pat. No. 5,510,118, which is specifically incorporated by reference, refers to a process using a Microfluidizer® resulting in nanoparticulate active agent particles.

Carvedilol can be added to a liquid media in which it is essentially insoluble to form a premix. The surface stabilizer can be present in the premix, it can be during particle size reduction, or it can be added to the drug dispersion following particle size reduction.

The premix can be used directly by subjecting it to mechanical means to reduce the average carvedilol particle size in the dispersion to the desired size, preferably less than about 5 microns. It is preferred that the premix be used directly when a ball mill is used for attrition. Alternatively, carvedilol and a surface stabilizer can be dispersed in the liquid media using suitable agitation, e.g., a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the carvedilol particle size conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the desired reduction in particle size. For media milling, the apparent viscosity of the premix is preferably from about 100 to about 1000 centipoise, and for ball milling the apparent viscosity of the premix is preferably from about 1 up to about 100 centipoise. Such ranges tend to afford an optimal balance between efficient particle size reduction and media erosion but are in no way limiting The attrition time can vary widely and depends primarily upon the particular mechanical means and processing conditions selected. For ball mills, processing times of up to five days or longer may be required. Alternatively, processing times of less than 1 day (residence times of one minute up to several hours) are possible with the use of a high shear media mill.

Preferably, the carvedilol particles are reduced in size at a temperature which does not significantly degrade carvedilol. Processing temperatures of less than about 30° to less than about 40° C. are ordinarily preferred. If desired, the processing equipment can be cooled with conventional cooling equipment. Control of the temperature, e.g., by jacketing or immersion of the milling chamber with a cooling liquid, is contemplated. Generally, the method of the invention is conveniently carried out under conditions of ambient temperature and at processing pressures which are safe and effective for the milling process. Ambient processing pressures are typical of ball mills, attritor mills, and vibratory mills.

Grinding Media

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. Zirconium oxide, such as 95% ZrO stabilized with magnesia, zirconium silicate, ceramic, stainless steel, titania, alumina, 95% ZrO stabilized with yttrium, and glass grinding media are exemplary grinding materials.

The grinding media can comprise particles that are preferably substantially spherical in shape, e.g., beads, consisting essentially of polymeric resin or glass or Zirconium Silicate or other suitable compositions. Alternatively, the grinding media can comprise a core having a coating of a polymeric resin adhered thereon.

In general, suitable polymeric resins are chemically and physically inert, substantially free of metals, solvent, and monomers, and of sufficient hardness and friability to enable them to avoid being chipped or crushed during grinding. Suitable polymeric resins include crosslinked polystyrenes, such as polystyrene crosslinked with divinylbenzene; styrene copolymers; polycarbonates; polyacetals, such as Delrin® (E.I. du Pont de Nemours and Co.); vinyl chloride polymers and copolymers; polyurethanes; polyamides; poly(tetrafluoroethylenes), e.g., Teflon® (E.I. du Pont de Nemours and Co.), and other fluoropolymers; high density polyethylenes; polypropylenes; cellulose ethers and esters such as cellulose acetate; polyhydroxymethacrylate; polyhydroxyethyl acrylate; and silicone-containing polymers such as polysiloxanes and the like. The polymer can be biodegradable. Exemplary biodegradable polymers include poly(lactides), poly(glycolide) copolymers of lactides and glycolide, polyanhydrides, poly(hydroxyethyl methacylate), poly(imino carbonates), poly(N-acylhydroxyproline)esters, poly(N-palmitoyl hydroxyproline) esters, ethylene-vinyl acetate copolymers, poly(orthoesters), poly(caprolactones), and poly(phosphazenes). For biodegradable polymers, contamination from the media itself advantageously can metabolize in vivo into biologically acceptable products that can be eliminated from the body. The polymeric resin can have a density from about 0.8 to about 3.0 g/cm$^3$.

The grinding media preferably ranges in size from about 0.01 to about 3 mm. For fine grinding, the grinding media is preferably from about 0.02 to about 2 mm, and more preferably from about 0.03 to about 1 mm in size.

In one embodiment of the invention, the carvedilol particles are made continuously. Such a method comprises continuously introducing carvedilol into a milling chamber, contacting the carvedilol with grinding media while in the chamber to reduce the carvedilol particle size, and continuously removing the nanoparticulate carvedilol from the milling chamber.

The grinding media can be separated from the milled nanoparticulate carvedilol using conventional separation techniques, in a secondary process such as by simple filtration, sieving through a mesh filter or screen, and the like. Other separation techniques such as centrifugation may also be employed. Alternatively, a screen can be utilized during the milling process to remove the grinding media following completion of particle size reduction.

F. Method of Treatment

The present invention is also directed to methods treatment or prevention using the nanoparticulate carvedilol compositions of the invention for conditions such as hypertension, congestive heart failure, cancer, viral infections, psychosis-related conditions such as tardive dyskinesia, tardive dystonia and tardive akathisia, and related conditions. In addition, the nanoparticulate carvedilol compositions of the invention are useful for improving the treatment of mental disorders in which dopamine blocking medications are used, such as manic episodes, major depressive episodes and psychoses, particularly schizophrenia and schizoaffective disorder.

For example, the nanoparticulate carvedilol compositions may be used to treat or prevent high blood pressure, congestive heart failure, and related conditions. In addition, the nanoparticulate carvedilol compositions may be used to treat a cancer, such as cancers of the colon, ovary, breast, prostate, pancreas, lung, melanoma, glioblastoma, oral cancer, and leukemias. The compositions of the invention are particularly useful in treating cancers mediated by epidermal growth factor and/or platelet derived growth of cancer cells, Protein kinase C (PKC) activity, and/or cyclooxygenase 2 enzyme.

Such treatment comprises administering to the subject the nanoparticulate carvedilol formulation of the invention. As used herein, the term "subject" is used to mean an animal, preferably a mammal, including a human or non-human. The terms patient and subject may be used interchangeably.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

One of ordinary skill will appreciate that effective amounts of carvedilol can be determined empirically and can be employed in pure form or, where such forms exist, in pharmaceutically acceptable salt, ester, or prodrug form. Actual dosage levels of carvedilol in the nanoparticulate compositions of the invention may be varied to obtain an amount of carvedilol that is effective to obtain a desired therapeutic response for a particular composition and method of administration. The selected dosage level therefore depends upon the desired therapeutic effect, the route of administration, the potency of the administered carvedilol the desired duration of treatment, and other factors.

Dosage unit compositions may contain such amounts of such submultiples thereof as may be used to make up the daily or other suitable dosing period (e.g., such as every other day, weekly, bi-weekly, monthly, etc.) It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

The following examples are given to illustrate the present invention. It should be understood, however, that the spirit and scope of the invention is not to be limited to the specific conditions or details described in these examples but should only be limited by the scope of the claims that follow. All references identified herein, including U.S. patents, are hereby expressly incorporated by reference.

Example 1

The purpose of this example was to prepare a nanoparticulate carvedilol formulation.

An aqueous dispersion of 5% (w/w) carvedilol (Verion, Inc. (Lionville, Pa.)) was combined with 1.25% (w/w) hydroxypropyl cellulose (HPC-SL) and 0.05% (w/w) dioctyl sodium sulfosuccinate (DOSS). This mixture was then milled in a roller mill (U.S. Stoneware, Mahwah, N.J.) using a 50% media load with 0.8 mm Yittium treated zirconia media (Tosoh, Ceramics Division) for 46 hours at 170 rpm.

Microscopy of the milled carvedilol sample, using a Lecia DM5000B and Lecia CTR 5000 light source (Laboratory Instruments and Supplies Ltd., Ashbourne Co., Meath, Ireland), showed well dispersed discrete particles. The sample appeared acceptable.

Following milling, the particle size of the milled carvedilol particles was measured, in deionized distilled water, using a Horiba LA 910 particle size analyzer. The mean milled carvedilol particle size was 160 nm, with a D90 of less than 228 nm. The pH of the nanoparticulate carvedilol dispersion was 9.6.

Following three days of storage at room temperature, the carvedilol particles remained in dispersion (i.e., no precipitation or crystal growth observed), with no visible particle size growth or agglomeration observed. After the three day period, the mean carvedilol particle size was 163 nm, with a D90 of less than 229 nm.

Stability of the nanoparticulate carvedilol dispersion was then measured in simulated biological fluids. For testing in simulated biological fluids, the composition was incubated at 40° C. for 1 hour in simulated gastric fluid (sodium chloride and pepsin in HCl and water), 0.01 N HCl (which simulates typical acidic conditions found in the stomach), and simulated intestinal fluid (Monobasic potassium phosphate, water, sodium hydroxide, and pancreatin). The results are show in Table 1, below.

TABLE 1

Stability of the Nanoparticulate Carvedilol Composition in Simulated Biological Fluids

| Composition | Simulated Gastric Fluid | 0.01 N HCl | Simulated Intestinal Fluid |
|---|---|---|---|
| 5% carvedilol 1.25% HPC-SL 0.05% DOSS | particle growth | acceptable | slight agglomeration |

The results demonstrate that the nanoparticulate carvedilol composition is stable at room temperature. Moreover, the composition does not exhibit significant particle size growth when incubated in simulated biological fluids. These results are predictive of excellent in vivo bioavailability.

Example 2

The purpose of this example was to prepare a nanoparticulate carvedilol formulation.

An aqueous dispersion of 5% (w/w) carvedilol (Verion, Inc. (Lionville, Pa.)) was combined with 1.25% (w/w) hydroxypropylmethyl cellulose (HPMC) and 0.05% (w/w) dioctyl sodium sulfosuccinate (DOSS). This mixture was then milled on a roller mill (U.S. Stoneware, Mahwah, N.J.), using 0.8 mm Yittrium treated zirconia attrition media (Tosoh, Ceramics Division) (50% media load). The mixture was milled at a speed of 170 rpms for 46 hours.

Microscopy of the nanoparticulate carvedilol sample, using a Lecia DM5000B. and Lecia CTR 5000 light source (Laboratory Instruments and Supplies Ltd., Ashbourne Co., Meath, Ireland), showed well dispersed discrete particles. The sample appeared acceptable.

Following milling, the particle size of the milled carvedilol particles was measured, in deionized distilled water, using a Horiba LA 910 particle size analyzer. The mean milled carvedilol particle size was 160 nm, with a D90 of less than 235 nm. The pH of the milled carvedilol dispersion was 9.8.

Following three days of storage at room temperature, the carvedilol particles remained in dispersion (i.e., no precipitation or crystal growth observed), with no visible particle size growth or agglomeration observed. After the three day period, the mean carvedilol particle size was 157 nm, with a D90 of less than 223 nm.

Stability of the nanoparticulate carvedilol dispersion was then measured in simulated biological fluids. For testing in simulated biological fluids, the composition was incubated at 40° C. for 1 hour in simulated gastric fluid (sodium chloride and pepsin in HCl and water), 0.01 N HCl (which simulates typical acidic conditions found in the stomach), and simulated intestinal fluid (Monobasic potassium phosphate, water, sodium hydroxide, and pancreatin). The results are show in Table 2, below.

TABLE 2

Stability of the Nanoparticulate Carvedilol Composition in Simulated Biological Fluids

| Composition | Simulated Gastric Fluid | 0.01 N HCl | Simulated Intestinal Fluid |
|---|---|---|---|
| 5% carvedilol 1.25% HPMC 0.05% DOSS | particle growth | acceptable | agglomeration |

The results demonstrate that the nanoparticulate carvedilol composition is stable at room temperature. Moreover, the composition does not exhibit significant particle size growth when incubated in simulated biological fluids, although the formulation prepared in Example 1 demonstrated less agglomeration when incubated in simulated intestinal fluid. These results are predictive of good in vivo bioavailability.

Example 3

The purpose of this example was to prepare a nanoparticulate carvedilol formulation.

An aqueous dispersion of 5% (w/w) carvedilol (Verion, Inc. (Lionville, Pa.)) was combined with 1.25% (w/w) polyvinylpyrrolidone (PVP) and 0.05% (w/w) dioctyl sodium sulfosuccinate (DOSS). This mixture was then milled on a roller mill (U.S. Stoneware, Mahwah, N.J.) using 0.8 mm Yittrium treated zirconia attrition media (Tosoh, Ceramics Division) (50% media load). The mixture was milled at a speed of 170 rpms for 5 days.

Microscopy of the milled carvedilol sample, using a Lecia DM5000B and Lecia CTR 5000 light source (Laboratory Instruments and Supplies Ltd., Ashbourne Co., Meath, Ireland), showed well dispersed discrete particles. The sample appeared acceptable.

Following milling, the particle size of the milled carvedilol particles was measured, in deionized distilled water, using a Horiba LA 910 particle size analyzer. The mean milled carvedilol particle size was 107 nm, with a D90 of less than 167 nm. The pH of the milled carvedilol dispersion was 9.2.

Stability of the nanoparticulate carvedilol dispersion was then measured in simulated biological fluids. For testing in simulated biological fluids, the composition was incubated at 40° C. for 1 hour in simulated gastric fluid (sodium chloride and pepsin in HCl and water), 0.01 N HCl (which simulates typical acidic conditions found in the stomach), and simulated intestinal fluid (Monobasic potassium phosphate, water, sodium hydroxide, and pancreatin). The results are show in Table 3, below.

TABLE 3

Stability of the Nanoparticulate Carvedilol
Composition in Simulated Biological Fluids

| Composition | Simulated Gastric Fluid | 0.01 N HCl | Simulated Intestinal Fluid |
|---|---|---|---|
| 5% carvedilol 1.25% PVP 0.05% DOSS | particle growth | acceptable | slight agglomeration |

The results demonstrate that the nanoparticulate carvedilol composition does not exhibit significant particle size growth when incubated in simulated biological fluids. These results are predictive of excellent in vivo bioavailability.

Example 4

The purpose of this example was to prepare a nanoparticulate carvedilol formulation.

An aqueous dispersion of 5% (w/w) carvedilol (Verion, Inc. (Lionville, Pa.)) was combined with 1.25% (w/w) Pluronic® S-630 (a random copolymer of vinyl acetate and vinyl pyrrolidone) and 0.05% (w/w) dioctyl sodium sulfosuccinate (DOSS). This mixture was then milled on a roller mill (U.S. Stoneware, Mahwah, N.J.) using 0.8 mm Yittrium treated zirconia attrition media (Tosoh, Ceramics Division) (50% media load). The mixture was milled at a speed of 170 rpms for 46 hours.

Microscopy of the nanoparticulate carvedilol sample, using a Lecia DM5000B and Lecia CTR 5000 light source (Laboratory Instruments and Supplies Ltd., Ashbourne Co., Meath, Ireland), showed well dispersed discrete particles. The sample appeared acceptable.

Following milling, the particle size of the milled carvedilol particles was measured, in deionized distilled water, using a Horiba LA 910 particle size analyzer. The mean milled carvedilol particle size was 189 nm, with a D90 of less than 279 nm. The pH of the milled carvedilol dispersion was 8.9.

Following three days of storage at room temperature, the carvedilol particles remained in dispersion (i.e., no precipitation or crystal growth observed), with no visible particle size growth or agglomeration observed. After the three day period, the mean carvedilol particle size was 160 nm, with a D90 of less than 224 nm.

Stability of the nanoparticulate carvedilol dispersion was then measured in simulated biological fluids. For testing in simulated biological fluids, the composition was incubated at 40° C. 1 hour in simulated gastric fluid (sodium chloride and pepsin in HCl and water), 0.01 N HCl (which simulates typical acidic conditions found in the stomach), and simulated intestinal fluid (Monobasic potassium phosphate, water, sodium hydroxide, and pancreatin). The results are show in Table 4, below.

TABLE 4

Stability of the Nanoparticulate Carvedilol
Composition in Simulated Biological Fluids

| Composition | Simulated Gastric Fluid | 0.01 N HCl | Simulated Intestinal Fluid |
|---|---|---|---|
| 5% carvedilol 1.25% S-630 0.05% DOSS | particle growth | acceptable | agglomeration |

The results demonstrate that the nanoparticulate carvedilol composition is stable at room temperature. Moreover, the composition does not exhibit significant particle size growth when incubated in simulated biological fluids, although the formulation prepared in Examples 1 and 3 demonstrated less agglomeration when incubated in simulated intestinal fluid. These results are predictive of good in vivo bioavailability.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A dispersion of a stable nanoparticulate carvedilol composition comprising:
    (a) a liquid dispersion medium;
    (b) particles of carvedilol, a salt thereof, or an optically active isomer thereof having an effective average particle size of less than about 2000 nm dispersed in the liquid dispersion medium; and
    (c) at least one surface stabilizer adsorbed on the surface of the carvedilol particles,
    wherein the surface stabilizer is free of intermolecular cross-linkage, and the liquid dispersion medium is water;
    wherein the carvedilol is in a crystalline phase;
    wherein at least about 70% of the carvedilol particles, by weight, have a particle size less than the effective average particle size;
    wherein carvedilol is present in an amount selected from the group consisting of from about 99.5% to about 0.001%, from about 95% to about 0.1%, and from about 90% to about 0.5%, by weight, based on the total combined weight of carvedilol; and
    wherein at least one surface stabilizer, not including other excipients; is present in an amount selected from the group consisting of from about 0.5% to about 99.999% by weight, from about 5.0% to about 99.9% by weight, and from about 10% to about 99.5% by weight, based on the total combined dry weight of carvedilol and at least one surface stabilizer, not including other excipients.

2. The dispersion of claim 1, wherein the effective average particle size of the nanoparticulate carvedilol particles is selected from the group consisting of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, and less than about 50 nm.

3. The dispersion of claim 2, wherein at least about 80%, at least about 90%, at least about 95%, or at least about 99% of the carvedilol particles, by weight, have a particle size less than the effective average particle size.

4. The dispersion of claim 1, wherein the carvedilol composition is formulated into a controlled release dosage form.

5. The composition dispersion of claim 1, wherein the composition further comprises one or more pharmaceutically acceptable excipients, carriers, or a combination thereof.

6. The composition dispersion of claim 1, wherein at least one surface stabilizer is selected from the group consisting of a non-ionic surface stabilizer, an anionic surface stabilizer, a cationic surface stabilizer, a zwitterionic surface stabilizer, and an ionic surface stabilizer.

7. The dispersion of claim 1, wherein at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-phospholipid, PEG-cholesterol, PEG-cholesterol derivative, PEG-vitamin A, PEG-vitamin E, random copolymers of vinyl acetate and vinyl pyrrolidone, a cationic polymer, a cationic biopolymer, a cationic polysaccharide, a cationic cellulosic, a cationic alginate, a cationic nonpolymeric compound, a cationic phospholipid, cationic lipids, polymethylmethacrylate trimethylammonium bromide, sulfonium compounds, polyvinylpyrrolidone-2-dimethylamino ethyl methacrylate dimethyl sulfate, hexadecyltrimethyl ammonium bromide, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium bromide, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$) dimethyl-benzyl ammonium chloride, N-tetradecylidmethylbenzyl ammonium chloride monohydrate, dimethyl didecyl ammonium chloride, N-alkyl and ($C_{12-14}$)dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts; amines, amine salts, amine oxides, imide azolinium salts, protonated quaternary acrylamides, methylated quaternary polymers, and cationic guar.

8. The dispersion of claim 1, wherein the AUC of carvedilol, when assayed in the plasma of a mammalian subject following administration, is greater than the AUC for a non-nanoparticulate carvedilol formulation, administered at the same dosage.

9. The dispersion of claim 1, wherein the $C_{max}$ of carvedilol, when assayed in the plasma of a mammalian subject following administration, is greater than the $C_{max}$ for a non-nanoparticulate carvedilol formulation, administered at the same dosage.

10. The dispersion of claim 1, wherein the $T_{max}$ of carvedilol, when assayed in the plasma of a mammalian subject following administration, is less than the $T_{max}$ for a non-nanoparticulate carvedilol formulation, administered at the same dosage.

11. The dispersion of claim 1, wherein the composition has the same rate of absorption when administered to a human under fed conditions as compared to fasting conditions.

12. The dispersion of claim 1, additionally comprising one or more non-carvedilol active agents.

13. The dispersion of claim 12, wherein the one or more non-carvedilol active agents is selected from the group consisting of antihypertensives, active agents useful in treating congestive heart failure, and active agents useful in treating cardiovascular disorders.

14. The dispersion of claim 12, wherein the one or more non-carvedilol active agents is selected from the group consisting of digoxin, nitrates, diuretics, beta blockers, alpha blockers, alpha-beta blockers, sympathetic nerve inhibitors, angiotensin converting enzyme (ACE) inhibitors, calcium channel blockers, and angiotensin receptor blockers.

15. A method of making a dispersion of a nanoparticulate carvedilol composition comprising:
  contacting particles of carvedilol, an optically active isomer thereof, or a salt thereof with at least one surface stabilizer in the presence of a liquid dispersion medium for a time and under conditions sufficient to provide a carvedilol composition having an effective average particle size of less than about 2 microns;
  wherein the surface stabilizer is adsorbed on the surface of the carvedilol particles, wherein the surface stabilizer is free of inter-molecular cross-linkages,
  wherein the liquid dispersion medium is water;
  wherein the carvedilol is in a crystalline phase;
  wherein at least about 70% of the carvedilol particles, by weight, have a particle size less than the effective average particle size;

wherein carvedilol is present in an amount selected from the group consisting of from about 99.5% to about 0.001%, from about 95% to about 0.1%, and from about 90% to about 0.5%, by weight, based on the total combined weight of carvedilol; and wherein at least one surface stabilizer, not including other excipients; is present in an amount selected from the group consisting of from about 0.5% to about 99.999% by weight, from about 5.0% to about 99.9% by weight, and from about 10% to about 99.5% by weight, based on the total combined dry weight of carvedilol and at least one surface stabilizer, not including other excipients.

16. The method of claim 15, wherein the contacting comprises grinding, wet grinding, homogenizing, or a combination thereof.

17. A method for treating or preventing hypertension comprising administering to a subject in need an effective amount of a composition dispersion comprising:
  (a) a liquid dispersion medium;
  (b) carvedilol nanoparticles having an effective average particle size of less than about 2 microns;
  (c) at least one surface stabilizer adsorbed on the surface of the carvedilol particles; and
  (d) at least one pharmaceutically acceptable carrier;
  wherein the surface stabilizer is free of inter-molecular cross-linkage;
  wherein the liquid dispersion medium is water
  wherein the carvedilol is in a crystalline phase;
  wherein at least about 70% of the carvedilol particles, by weight, have a particle size less than the effective average particle size;
  wherein carvedilol is present in an amount selected from the group consisting of from about 99.5% to about 0.001%, from about 95% to about 0.1%, and from about 90% to about 0.5%, by weight, based on the total combined weight of carvedilol; and
  wherein at least one surface stabilizer, not including other excipients; is present in an amount selected from the group consisting of from about 0.5% to about 99.999% by weight, from about 5.0% to about 99.9% by weight, and from about 10% to about 99.5% by weight, based on the total combined dry weight of carvedilol and at least one surface stabilizer, not including other excipients.

18. A method for treating congestive heart failure comprising administering to a subject in need an effective amount of a composition comprising:
  (a) a liquid dispersion medium;
  (b) carvedilol nanoparticles having an effective average particle size of less than about 2 microns;
  (c) at least one surface stabilizer adsorbed on the surface of the carvedilol particles; and
  (d) at least one pharmaceutically acceptable carrier;
  wherein the surface stabilizer is free of inter-molecular cross-linkages;
  wherein the liquid dispersion medium is water;
  wherein the carvedilol is in a crystalline phase;
  wherein at least about 70% of the carvedilol particles, by weight, have a particle size less than the effective average particle size;
  wherein carvedilol is present in an amount selected from the group consisting of from about 99.5% to about 0.001%, from about 95% to about 0.1%, and from about 90% to about 0.5%, by weight, based on the total combined weight of carvedilol; and
  wherein at least one surface stabilizer, not including other excipients; is present in an amount selected from the group consisting of from about 0.5% to about 99.999% by weight, from about 5.0% to about 99.9% by weight, and from about 10% to about 99.5% by weight, based on the total combined dry weight of carvedilol and at least one surface stabilizer, not including other excipients.

19. The dispersion of claim 1, wherein the surface stabilizer is selected from the group consisting of hydroxypropyl cellulose, dioctyl sodium sulfosuccinate, hydroxypropylmethyl cellulose, polyvinylpyrrolidone, a random copolymer of vinyl acetate and vinyl pyrrolidone.

20. The method of claim 15, the surface stabilizer is selected from the group consisting of hydroxypropyl cellulose, dioctyl sodium sulfosuccinate, hydroxypropylmethyl cellulose, polyvinylpyrrolidone, and a random copolymer of vinyl acetate and vinyl pyrrolidone.

21. The method of claim 17, wherein the surface stabilizer is selected from the group consisting of hydroxypropyl cellulose, dioctyl sodium sulfosuccinate, hydroxypropylmethyl cellulose, polyvinylpyrrolidone, and a random copolymer of vinyl acetate and vinyl pyrrolidone.

22. The method of claim 18, wherein the surface stabilizer is selected from the group consisting of hydroxypropyl cellulose, dioctyl sodium sulfosuccinate, hydroxypropylmethyl cellulose, polyvinylpyrrolidone, and a random copolymer of vinyl acetate and vinyl pyrrolidone.

* * * * *